United States Patent
Abi Georges et al.

(10) Patent No.: US 10,794,897 B2
(45) Date of Patent: Oct. 6, 2020

(54) SYSTEM AND METHODS FOR PREDICTING DRUG-INDUCED INOTROPIC AND PRO-ARRHYTHMIA RISK

(71) Applicant: AnaBios Corporation, San Diego, CA (US)

(72) Inventors: Najah Elias Abi Georges, San Diego, CA (US); Andrea Piero Ghetti, San Diego, CA (US); Paul Edward Miller, San Diego, CA (US)

(73) Assignee: AnaBios Corporation, San Diego, CA (US)

( * ) Notice: Subject to any disclaimer, the term of this patent is extended or adjusted under 35 U.S.C. 154(b) by 0 days.

(21) Appl. No.: 15/886,742

(22) Filed: Feb. 1, 2018

(65) Prior Publication Data

US 2018/0224427 A1 Aug. 9, 2018

Related U.S. Application Data

(60) Provisional application No. 62/454,786, filed on Feb. 4, 2017.

(51) Int. Cl.
| | |
|---|---|
| *A61B 5/0452* | (2006.01) |
| *A61B 5/00* | (2006.01) |
| *G16H 50/30* | (2018.01) |
| *A61B 5/0402* | (2006.01) |
| *G01N 33/50* | (2006.01) |
| *G01N 33/68* | (2006.01) |
| *G16H 50/20* | (2018.01) |
| *A61B 5/11* | (2006.01) |

(52) U.S. Cl.
CPC ....... *G01N 33/5008* (2013.01); *A61B 5/0402* (2013.01); *A61B 5/0452* (2013.01); *A61B 5/4836* (2013.01); *A61B 5/7275* (2013.01); *A61B 5/746* (2013.01); *G01N 33/6887* (2013.01); *G16H 50/20* (2018.01); *G16H 50/30* (2018.01); *A61B 5/1107* (2013.01); *A61B 2562/0252* (2013.01); *G01N 2800/326* (2013.01)

(58) Field of Classification Search
None
See application file for complete search history.

(56) References Cited

U.S. PATENT DOCUMENTS

| | | |
|---|---|---|
| 2009/0298795 A1 | 12/2009 | Paolocci et al. |
| 2011/0144125 A1 | 6/2011 | Wolkowicz |
| 2011/0318775 A1 | 12/2011 | Mercola et al. |
| 2012/0107861 A1 | 5/2012 | Abrams et al. |
| 2014/0363841 A1 | 12/2014 | Shim et al. |
| 2016/0177308 A1 | 6/2016 | Bowser et al. |
| 2016/0186139 A1 | 6/2016 | Regnier et al. |
| 2016/0220225 A1 | 8/2016 | Wang et al. |

OTHER PUBLICATIONS

Pointon et al. (Toxicological Sciences (2015) vol. 144:227-237).*
Butler et al. (Toxicological Sciences (2015) vol. 145:396-406).*
Harmer et al. (Toxicology and Applied Pharmacology (2012) vol. 260:162-172).*
Van der Velden et al. (Cardiovascular Research (1998) vol. 38:414-423).*
Harmer et al. "Validation of an in vitro contractility assay using canine ventricular myocytes" Toxicology and Applied Pharmacology 260 (2012) 162-172.
International Search Report and Written Opinion, PCT/US2018/016504, dated Apr. 23, 2018.

* cited by examiner

*Primary Examiner* — Lori A. Clow
(74) *Attorney, Agent, or Firm* — Entralta P.C.; Justin G. Sanders; Peter D. Weinstein

(57) ABSTRACT

A drug-induced risk prediction system and associated methods are disclosed for predicting at least one of a drug-induced inotropic risk and a pro-arrhythmia risk in connection with an at least one drug, based on a select at least one contractility parameter associated with an at least one heart.

8 Claims, 2 Drawing Sheets

SYSTEM AND METHODS FOR PREDICTING DRUG-INDUCED INOTROPIC AND PRO-ARRHYTHMIA RISK

RELATED APPLICATIONS

This application claims priority and is entitled to the filing date of U.S. provisional application Ser. No. 62/454,786, filed on Feb. 4, 2017. The contents of the aforementioned application are incorporated herein by reference.

BACKGROUND

The subject of this provisional patent application relates generally to drug safety, and more particularly to a system and associated methods for predicting at least one of a drug-induced inotropic risk and a pro-arrhythmia risk.

Applicant(s) hereby incorporate herein by reference any and all patents and published patent applications cited or referred to in this application.

By way of background, cardiac safety remains one of the leading causes of drug development discontinuation and withdrawal from the market. Pro-arrhythmic drugs often induce prolongation of the QT interval on an electrocardiogram and can lead to polymorphic ventricular tachycardia. This kind of pro-arrhythmic liability has led to the withdrawal from the market of a wide variety of therapeutics. Additionally, drug-induced effects on cardiac contractility can limit the tolerated dose and therefore impact on efficacy and utility of therapies. For example, many oncology drugs are associated with a risk of decreased left ventricular ejection fraction. Furthermore, compromised left ventricular ejection fraction can progress to heart failure and in some cases death. Drugs that increase cardiac contractility may also raise safety concerns. For example, positive inotropic drugs used to treat heart failure by prolonging the cardiomyocyte cytosolic cyclic AMP signal have been shown to increase mortality. In light of drug-induced cardiotoxicity events, the reliability of current preclinical safety testing paradigms has been questioned, which has led to demands for more predictive tools and novel analytical biomarkers.

The excitation-contraction coupling, which results from the coupling of the cardiac tissue's electrical excitation (action potential) and the consequent mechanical contraction (inotropy), is a fundamental property of normal heart function. Depolarization and repolarization of the membrane potential are electrochemical changes happening in cardiomyocytes of the heart during a cardiac cycle, while contraction and relaxation of cardiomyocytes are the mechanical changes associated with the same cardiac cycle. Action potentials and the consequent changes in intracellular calcium concentration are directly related to contraction. Due to depolarization of cardiomyocytes, an action potential is generated, which leads to intracellular calcium increase, which leads to the contraction of cardiomyocytes. Repolarization of the action potential restores the original electrical conditions of the cell, returns the intracellular calcium to the resting level and produces the relaxation of the cardiomyocyte.

While the electrochemical and mechanical transients associated with the cardiomyocytes activity cycle are mechanistically related, the measurement of the two classes of transients requires very different sets of methods and instruments. Electrochemical changes (the cardiac action potential) are recorded using electrophysiology based methods relying on the measurement and amplification of changes in the ionic concentrations and/or electrical field potentials, that are associated with the opening and closing of voltage-gated ion channels located on the surface of the cardiomyocytes. The mechanical transient associated with contraction-relaxation, can be recorded using force transducers or, more simply, tracking the cardiomyocyte morphological changes using edge detection and bright field microscopy. In practical terms, the measurement of contraction/relaxation and the related mechanical changes, provides high information content and is an order of magnitude simpler (low technical complexity, no use of cytotoxic reagents) to implement than the measurement of the electrochemical transients. The methods available for this kind of measurement are also more easily adapted to higher throughput modalities and the instruments required are typically less expensive compared to the ones used for electrophysiology-based measurements.

In the context of pharmaceutical drug safety assessment, it is important to determine the potential toxicity risks posed in both the electrochemical as well as the mechanical domain. The ideal method would enable the measurement of both action potential and contraction/relaxation in cardiomyocytes exposed to a drug. An alternative, and highly desirable solution, would rely on the simple measurement of the contraction/relaxation parameters, and the algorithmic derivation of the correlated electrochemical transients. This would enable the direct measurement of contractility-related (inotropic) toxicities, the algorithmic calculation of the pro-arrhythmic risk that might result for alteration of the electrochemical and/or intracellular calcium transients, and the potential for deconvoluting finger-printing mechanism(s) of action and investigation of drug structure-activity relationships.

Aspects of the present invention fulfill these needs and provide further related advantages as described in the following summary.

SUMMARY

Aspects of the present invention teach certain benefits in construction and use which give rise to the exemplary advantages described below.

The present invention solves the problems described above by providing a drug-induced risk prediction system and associated methods for predicting at least one of a drug-induced inotropic risk and a pro-arrhythmia risk in connection with an at least one drug, based on a select at least one contractility parameter associated with an at least one heart. In at least one embodiment, an at least one computing device is configured for receiving and processing select data obtained by an at least one monitoring device positioned and configured for obtaining data related to the at least one heart. After the at least one drug has been administered to the at least one heart, and once it is determined that the at least one drug has taken appropriate effect on the at least one heart, if the at least one heart consists of cell-based assays, the computing device obtains at multiple pre-determined intervals for a pre-determined period of time, via the at least one monitoring device, at least one contractility parameter comprising cardiomyocyte contractility transients including at least one of a fractional sarcomere shortening ("$S_{FS}$"), a time to 90% relaxation ("$TR_{90}$"), an after-contraction ("AC"), a contractility escape type 1 ("CE1"), and a contractility escape type 2 ("CE2"). Alternatively, if the at least one heart consists of organ-based or tissue-based assays, the computing device obtains at multiple pre-determined intervals for a pre-determined period of time, via the at least one monitoring device, at least one contractility parameter related to trabeculae force of contraction including at least one of a maximum amplitude of force of contraction ("MAC"), a time to 70% relaxation ("$TR_{70}$"), a time to 90% relaxation ("$TR_{90}$"), an after-contraction ("AC"), and a contraction escape ("CE"). The computing device then calculates a delta for each of the at least one obtained contractility parameter. Upon determining that a pre-determined number of the at least one obtained contractility parameter each has a delta that equals or exceeds the associated at least one risk threshold value, the computing device concludes that there is at least one of a drug-induced inotropic risk and a pro-arrhythmia risk in connection with the at least one drug. Otherwise, upon determining that a pre-determined number of the at least one obtained contractility parameter each has a delta that is less than the associated at least one risk threshold value, the computing device concludes that there is likely an absence of at least one of a drug-induced inotropic risk and a pro-arrhythmia risk in connection with the at least one drug.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

Figure 1:
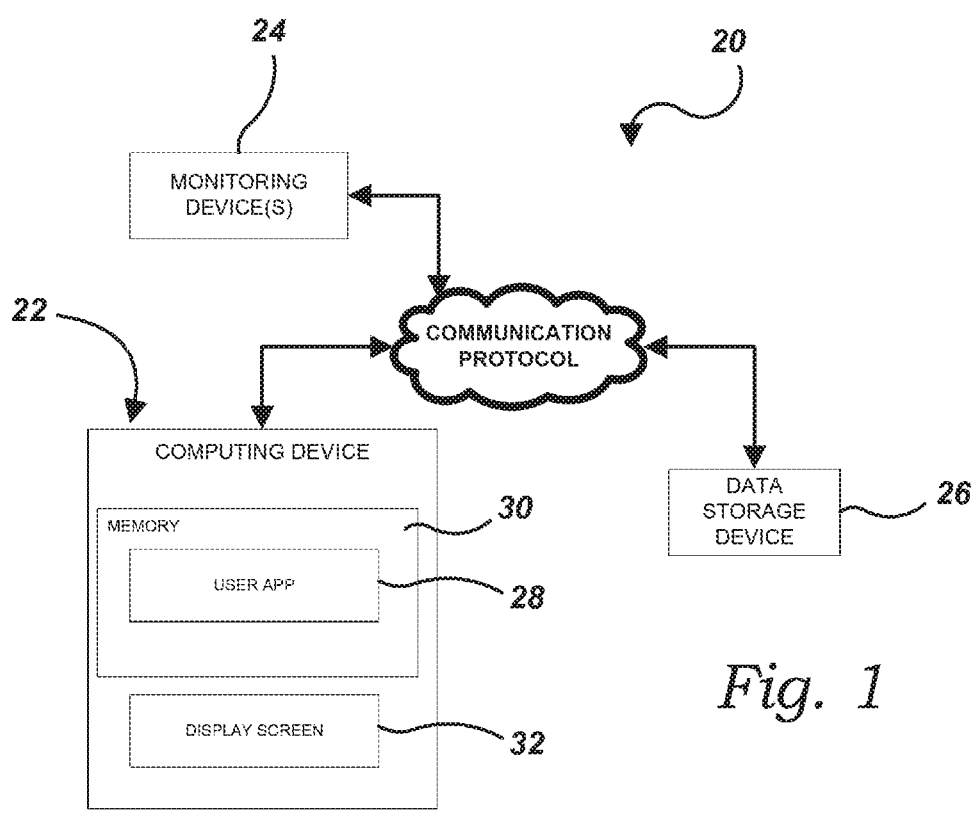
FIG. 1 is a simplified schematic view of an exemplary drug-induced risk prediction system, in accordance with at least one embodiment.

Turning now to FIG. 1, there is shown a simplified schematic view of an exemplary drug-induced risk prediction system 20 configured for predicting at least one of drug-induced inotropic and pro-arrhythmia risk in connection with an at least one drug to be tested. In at least one embodiment, as discussed further below, given that a T-wave recorded in an electrocardiogram ("ECG") represents ventricular repolarization and is therefore an electrical marker of the beginning of cardiac relaxation at the end of the contraction phase of a heartbeat, the system 20 leverages this correlation in reverse and uses the parameters of contractility transients to provide a novel analytical approach to derive the effects of drugs on the cardiac action potential.

Accordingly, in at least one embodiment, the system 20 provides an at least one computing device 22 configured for receiving and processing select data obtained by an at least one monitoring device 24 positioned and configured for obtaining data related to an at least one heart. In that regard, it should be noted that in at least one embodiment, the at least one heart is at least one of an ex vivo isolated heart, an isolated sample of cardiac tissue (such as ventricular trabeculae, for example), and isolated cardiomyocytes (such as ventricular myocytes, for example). As discussed further below, in at least one embodiment, the at least one monitoring device 24 includes an ECG device positioned and configured for obtaining electrical activity (such as the cardiac action potential, for example) associated with the at least one heart. In at least one further embodiment, the at least one monitoring device 24 includes a current amplifier device positioned and configured for obtaining electrical activity associated with the at least one heart. In at least one further embodiment, the at least one monitoring device 24 includes a force transducer device positioned and configured for obtaining force activity associated with the at least one heart. Additionally, in at least one embodiment, the at least one monitoring device 24 includes an optical device positioned and configured for obtaining visual data associated with contractions of the at least one heart. In further embodiments, the at least one monitoring device 24 may include any other type of device, sensor, or combination thereof—now known or later developed—capable of substantially carrying out the functionality described herein. In at least one embodiment, the computing device 22 and the at least one monitoring device 24 are one and the same—as such, it is intended that those terms as used herein are to be interchangeable with one another. In at least one embodiment, the system 20 further provides an at least one data storage device 26 in selective communication with the computing device 22 and configured for storing said data obtained by the at least one monitoring device 24 and processed by the computing device 22, along with certain other data as discussed further below. In at least one embodiment, the computing device 22 and data storage device 26 are also one and the same—as such, it is intended that those terms as used herein are to be interchangeable with one another as well.

At the outset, it should be noted that communication between each of the at least one computing device 22, at least one monitoring device 24, and at least one data storage device 26 may be achieved using any wired- or wireless-based communication protocol (or combination of protocols) now known or later developed. As such, the present invention should not be read as being limited to any one particular type of communication protocol, even though certain exemplary protocols may be mentioned herein for illustrative purposes. It should also be noted that the term "computing device" is intended to include any type of computing or electronic device, now known or later developed, capable of substantially carrying out the functionality described herein—such as desktop computers, mobile phones, smartphones, laptop computers, tablet computers, personal data assistants, gaming devices, wearable devices, etc. As such, the system 20 should not be read as being limited to use with any one particular type of computing or electronic device, even though certain exemplary devices may be mentioned or shown herein for illustrative purposes.

In at least one embodiment, the computing device 22 contains the hardware and software necessary to carry out the exemplary methods for predicting at least one of drug-induced inotropic and pro-arrhythmia risk, as described herein. Furthermore, in at least one embodiment, the computing device 22 comprises a plurality of computing devices selectively working in concert with one another to carry out the exemplary methods for predicting at least one of drug-induced inotropic and pro-arrhythmia risk, as described herein. In at least one embodiment, the computing device 22 provides a user application 28 residing locally in memory 30 on the computing device 22, the user application 28 being configured for selectively communicating with the at least one monitoring device 24, as discussed further below. It should be noted that the term "memory" is intended to include any type of electronic storage medium (or combination of storage mediums) now known or later developed, such as local hard drives, RAM, flash memory, secure digital ("SD") cards, external storage devices, network or cloud storage devices, integrated circuits, etc. In at least one embodiment, the computing device 22 provides an at least one display screen 32 configured for displaying select data, as discussed in detail below. In at least one such embodiment, the display screen 32 is a touchscreen.

In use, in at least one embodiment, the system 20 is capable of predicting at least one of drug-induced inotropic and pro-arrhythmia risk in connection with an at least one drug to be tested. Specifically, the potential for the at least one drug to induce electrochemical disturbances that pose a pro-arrhythmic risk is calculated based on changes observed by the system 20 in connection with select contractility parameters associated with the at least one heart. In a bit more detail, in at least one embodiment, as illustrated in the flow diagram of FIG. 2, after the at least one drug is administered to the at least one heart (202), the user application 28 waits an appropriate period of time for the at least one drug to take appropriate effect (204). In at least one embodiment, the user application 28 waits until the at least one drug has reached its plateau effect; however, in further embodiments, other appropriate periods of time may be substituted. The user application 28 also determines the specifics of the at least one heart (206)—specifically, determining whether the at least one heart consists of cell-based assays (such as isolated cardiomyocytes, for example) or organ-based or tissue-based assays (such as ex vivo hearts or isolated cardiac tissue, for example)—so as to determine an appropriate at least one parameter to monitor in the at least one heart (208).

In at least one embodiment, where the at least one heart consists of cell-based assays, the at least one parameter obtained by the user application 28 (via the appropriate at least one monitoring device 24) comprise cardiomyocyte contractility transients including at least one of a fractional sarcomere shortening ("$S_{FS}$"), a time to 90% relaxation ("$TR_{90}$"), an after-contraction ("AC"), a contractility escape type 1 ("CE1"), and a contractility escape type 2 ("CE2"). In a bit more detail, in at least one embodiment, the fractional sarcomere shortening parameter—i.e., the shortening or contracting of heart muscle—is used as a marker of inotropy; the time to 90% relaxation parameter is used as a marker to estimate the potential for drug-induced action or QT prolongation; the after-contraction parameter is used as a marker to assess drug-induced pro-arrhythmia, and is directly correlated to the spontaneous depolarization of the cardiomyocyte, which leads to an abnormal and unsynchronized contraction; the contractility escape type 1 parameter—i.e., an electrical stimulus that does not trigger a normal cardiomyocyte contraction—is used as a marker to assess drug-induced pro-arrhythmia; and the contractility escape type 2 parameter—i.e., an electrical stimulus that does not trigger a normal beat after full relaxation of cardiomyocyte contraction—is used as a marker to assess drug-induced suppression of cardiomyocyte depolarization and can predict the inhibitory effect of drugs on cardiac $Ca^{2+}$, $Na^+$ and/or $K^+$ channels. In addition to $S_{FS}$, other parameters of cardiomyocyte contractility transients including at least one of a peak height, maximum contraction velocity (the percentage of the shortening or contracting of heart muscle), maximum contraction velocity time, maximum relaxation velocity (the maximum rate at which the shortening or contracting heart muscle relaxes), maximum relaxation velocity time, time to peak, time to 10% peak and time to 50% peak are used as markers to detect the different profiles of inotropic drugs and illustrate finger-printing different mechanisms of action that include those involving ion channels, pumps, enzymes, $Ca^{2+}$ handling and contractile proteins. In still further embodiments, additional new parameters, now known or later conceived, may be added and still form a construct within the scope of the present invention.

In at least one embodiment, where the at least one heart consists of organ-based or tissue-based assays, the at least one parameter obtained by the user application 28 (via the appropriate at least one monitoring device 24) comprise parameters related to trabeculae force of contraction including at least one of a maximum amplitude of force of contraction ("MAC"), a time to 70% or 90% relaxation ("$TR_{70}$" or "$TR_{90}$"), an after-contraction ("AC") and contraction escape ("CE"). In a bit more detail, in at least one embodiment, the maximum amplitude of force of contraction parameter is used as a marker of inotropy; the time to 70% or 90% relaxation parameter is used as a marker to estimate the potential for drug-induced action or QT prolongation; and the after-contraction and contraction escape parameters are used as markers to assess drug-induced pro-arrhythmia and suppression of cardiac depolarization, respectively. In addition to MAC, other parameters of transients of the force of contraction—including at least one of peak amplitude, amplitude height, time to peak, rise time, fall time, rise slope, fall slope, maximum slope and minimum slope—are used as markers to detect the different profiles of inotropic drugs and illustrate finger-printing different mechanisms of action that include those involving ion channels, pumps, enzymes, $Ca^{2+}$ handling and contractile proteins. In still further embodiments, additional new parameters, now known or later conceived, may be added and still form a construct within the scope of the present invention.

In at least one embodiment, the at least one parameter obtained by the user application 28 (via the appropriate at least one monitoring device 24) may further comprise at least one of a time to reaction ("TR") instability, a TR triangulation, a short-term variability ("STV") of TR, a TR alternans, a maximum TR dispersion, and an effective refractory period ("ERP") of TR. In a bit more detail, in at least one embodiment, the time to reaction instability parameter is calculated as the standard deviation ("SD") of a pre-determined number of consecutive TRs (such as 3 to 300 TRs, for example); the TR triangulation parameter is calculated as the ratio of $$\frac{TR_{90}}{TR_{50}} \text{ or } \frac{TR_{90} - TR_{30}}{TR_{90}},$$

and the difference of $TR_{90} - TR_{30}$ is analyzed to describe the triangulation of the contractility signal; the STV of TR parameter is the beat-to-beat variability of relaxation, and is calculated as STV from TR Poincaré plots over a period of thirty seconds, such that STV for all TRs is calculated as $$STV = \sum \frac{|TR_{n+1} - TR_n|}{(30 \times \sqrt{2})},$$

where $TR_n$ and $TR_{n+1}$ are the TRs for the nth contraction signals and the following one, respectively; the TR alternans parameter is calculated as the TR difference for successive odd and even TRs in consecutive contractility transients of a pre-determined amount (such as 30 consecutive transients, for example, though any other number may be utilized); the maximum TR dispersion parameter is calculated as the difference between a maximum TR and a minimum TR for consecutive contractility transients of a pre-determined amount (such as 30 consecutive transients, for example, though any other number may be utilized); and the ERP of TR parameter is the ratio of $$\frac{TR_{50} - TR_{20}}{TR_{50}}$$

and describes the ERP of the contractility signal.

Figure 2:
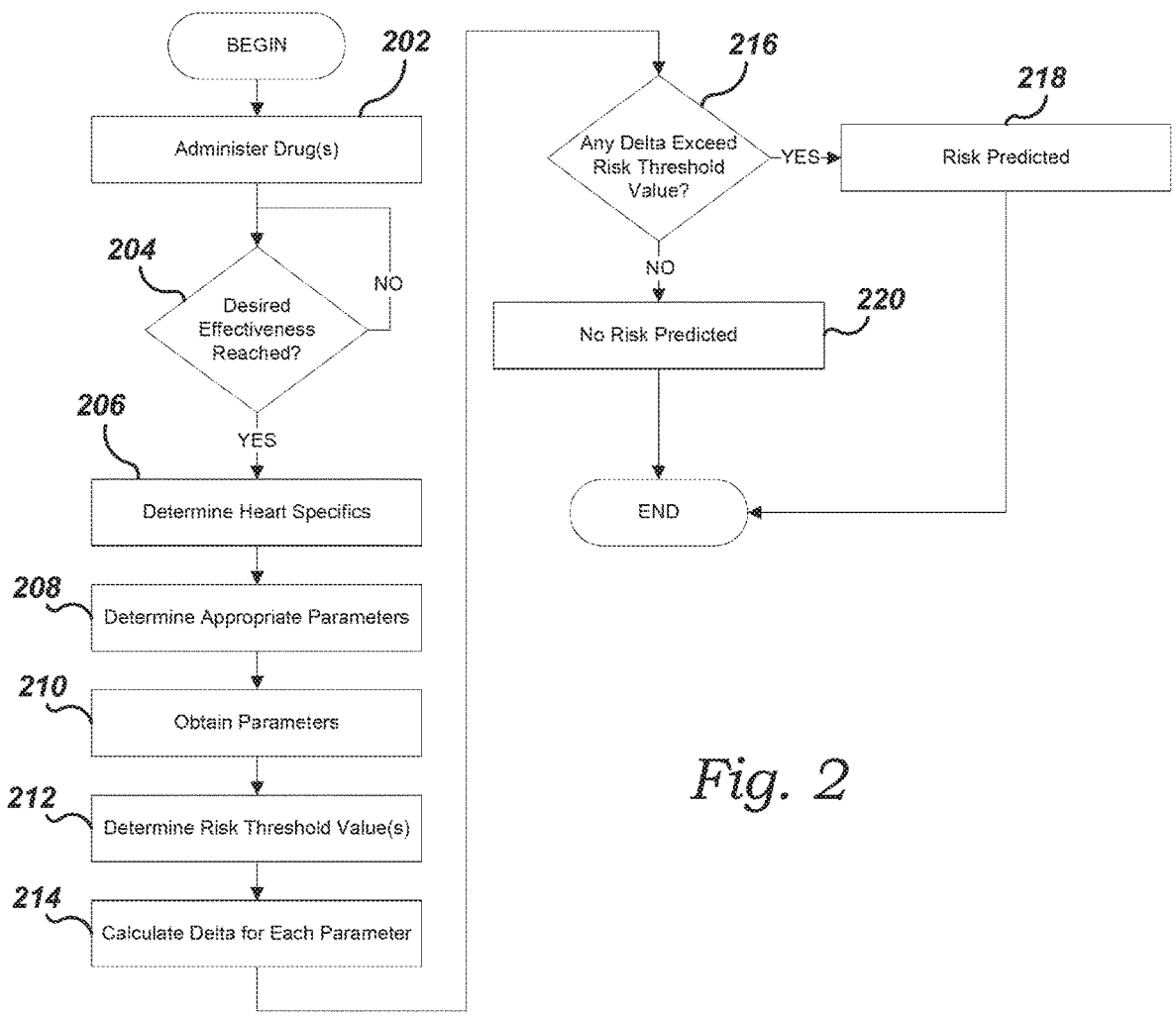
FIG. 2 is a flow diagram of an exemplary method for predicting at least one of drug-induced inotropic and pro-arrhythmia risk, in accordance with at least one embodiment.

With continued reference to FIG. 2, in at least one embodiment, the user application 28 obtains the appropriate parameters via the at least one monitoring device 24 at multiple pre-determined intervals for a pre-determined period of time (210). For example, in at least one embodiment, the parameters are obtained from a set of between five and 120 consecutive transients (such as fifteen, for example); however, in further embodiments, any number of consecutive transients may be used—dependent, at least in part, on at least one of the type of drug being tested, the age of the intended drug user, the gender of the intended drug user, the desired sensitivity and/or specificity of the prediction, etc. In at least one embodiment, the user application 28 also determines an appropriate at least one risk threshold value (212) based on one or more factors, including but not limited to the type of drug being tested, the age of the intended drug user, the gender of the intended drug user, the desired sensitivity and/or specificity of the prediction, etc. In at least one embodiment, the at least one risk threshold value may range between 0% and 100%—for example, 15%.

Upon obtaining the appropriate parameters and determining the appropriate at least one risk threshold value, the user application 28 calculates a change (or delta "Δ") for each parameter (214). Thus, for example, where the at least one heart consists of cell-based assays, the user application 28 calculates at least one of $\Delta S_{FS}$, $\Delta TR_{90}$, $\Delta AC$, $\Delta CE1$, and $\Delta CE2$. Similarly, where the at least one heart consists of organ-based or tissue-based assays, the user application 28 calculates at least one of $\Delta MAC$, $\Delta TR_{70}$, $\Delta TR_{90}$ and $\Delta AC$. The user application 28 then determines whether any of the obtained parameters has a delta that equals or exceeds the associated at least one risk threshold value (216). In that regard, it should be noted that in at least one embodiment, each parameter may have its own individual risk threshold value. For example, in at least one such embodiment, $\Delta AC$, $\Delta CE1$ and/or $\Delta CE2$ each has a risk threshold value of 7%, while $\Delta S_{FS}$ and $\Delta TR_{90}$ each has a risk threshold value of 10%. In at least one embodiment, upon determining that at least one of the obtained parameters has a delta that equals or exceeds the associated at least one risk threshold value, the user application 28 concludes that there is a drug-induced inotropic and pro-arrhythmia risk in connection with the at least one drug being tested (218); otherwise, the user application 28 determines that there is likely no drug-induced inotropic and pro-arrhythmia risk (220). In at least one further embodiment, the user application 28 will conclude that there is a drug-induced inotropic and pro-arrhythmia risk in connection with the at least one drug being tested upon determining that a pre-determined number of obtained parameters (rather than a single parameter)—or, alternatively, a particular combination of obtained parameters—each has a delta that equals or exceeds the associated at least one risk threshold value. In at least one embodiment, it is expected that the most reliable predictions will be affected when the user application 28 determines that the $\Delta AC$, $\Delta CE1$, or $\Delta CE2$ exceeds the associated risk threshold value.

Thus, in at least one embodiment, the system 20 provides a novel approach that aligns with the critical needs expressed by both regulators and industry leaders and allows the simultaneous prediction of drug-induced inotropic and pro-arrhythmia risk.

EXAMPLES

The following non-limiting examples are provided for illustrative purposes only, in order to facilitate a more complete understanding of representative embodiments now contemplated. These examples are intended to be a mere subset of all possible contexts in which the system 20 may be utilized. Thus, these examples should not be construed to limit any of the embodiments described in the present specification. Ultimately, the system 20 may be utilized in virtually any context where predicting at least one of drug-induced inotropic and pro-arrhythmia risk is desired.

The relevance of the system 20 in connection with human cardiomyocyte preparation was validated with a set of thirty-eight reference drugs with well characterized clinical outcomes. Both positive and negative pro-arrhythmic controls were used, including twenty-three torsadogenic (like clarithromycin, cisapride, d,l-sotalol, dofetilide, domperidone, quinidine) and ten non-torsadogenic drugs (like mexiletine, ranolazine, verapamil), and five positive inotropic drugs (isoproterenol, β-adrenoceptor agonist; milrinone, type 3 phosphodiesterase inhibitor; digoxin, $Na^+/K^+$ pump inhibitor; omecamtiv mecarbil, myosin activator; levosimendan, $Ca^{2+}$ sensitizer). Through these validation exercises, the system 20, for example, was able to predict QT/pro-arrhythmic potential (concentration-dependent increases in AC incidence, CE and prolongation of $TR_{90}$) of quinidine starting at the free Effective Therapeutic Plasma Concentration ("fETPC") and the safety of verapamil up to 222-fold the fETPC (neither AC or CE incidence, no change in $TR_{90}$). Additionally, the system 20 demonstrated the inability of the dog cardiomyocyte model to accurately predict the cardiac risk and safety of quinidine and verapamil, respectively.

The system 20, for example, was also able to predict the pro-arrhythmic potential of other positive controls. For example, AC incidence with cisapride and domperidone was seen starting at the fETPC, while sotalol, dofetilide and clarithromycin-induced ACs starting at 10-fold the fETPC. Moreover, all of these five torsadogenic drugs induced only CE1 events. In contrast, non-torsadogenic compounds, like mexiletine and ranolazine, induced no ACs up to the highest multiple of fETPCs tested in the evaluation (30× and 100×, respectively). Additionally, these two non-torsadogenic drugs did not induce CE1 events and were associated only with incidence of CE2, in line with their known effects $Na^+$ and $Ca^{2+}$ channels. Finally, all five positive and two negative controls increased $TR_{90}$ in a concentration-dependent manner and therefore their QT-prolonging effect could also be predicted using the present method. When drug pro-arrhythmic activity was evaluated at 10-fold of the fETPC of the thirty-three positive and negative controls, the AC parameter had excellent sensitivity and specificity values of 96% and 100%, respectively. The high predictivity strongly suggests that the method described herein, in at least one embodiment, can differentiate between drugs associated with high and low pro-arrhythmic risk. The ability of the AC parameter to respond differently to perturbations introduced by pro-arrhythmic vs. non-pro-arrhythmic drugs, in at least one embodiment, constitutes a critical finding of the system 20 and confirms the translational safety potential of this marker. In addition to assessing pro-arrhythmic potential of drugs, the contractility data also allowed the evaluation of the inotropic potential of thirty-three reference drugs. It was found that selective hERG channel blockers, like dofetilide and sotalol, have no effects on sarcomere shortening, while multi-channel blockers, like cisapride, clarithromycin, domperidone, mexiletine and ranolazine, inhibited sarcomere shortening. These data clearly demonstrate the ability of the system 20 to identify drugs associated with negative inotropic risk, in at least one embodiment. Moreover, data obtained with the system 20 demonstrate its ability to identify drugs associated with positive inotropic effects, in at least one embodiment. It was also found that effects of these five positive inotropes on contractility transient parameters illustrate the ability of system 20 for finger-printing different mechanisms of action, in at least one embodiment. For example, while isoproterenol and levosimendan increased $F_{SF}$, peak height, maximum contraction velocity and maximum relaxation velocity with no effects on time to peak and maximum relaxation velocity time and no CE incidence, both drugs affected differently maximum contraction velocity time (increased by isoproterenol with levosimendan had no effect), time to 10% & 50% peaks and $TR_{90}$ (decreased by isoproterenol with levosimendan had no effect) and AC incidence at 10-fold the fETPC (isoproterenol induced no AC while levosimendan did).

The relevance and predictivity of the system 20 and associated methods of use in the ex vivo human ventricular trabeculae preparation was also confirmed with a set of four reference drugs. The drug set included a sympathomimetic (isoproterenol), a non-torsadogenic (verapamil) and two torsadogenic (dofetilide and sotalol) compounds. It was found that dofetilide and sotalol had no effects on MAC, while isoproterenol increased MAC (by 315% at 0.03 μM) and verapamil decreased it (IC50=1.46 μM). AC incidence with dofetilide and sotalol was observed starting at the fETPC, while verapamil and isoproterenol did not induce any ACs even when tested up to 222× and 1000× of their fETPCs, respectively. Finally, concentration-dependent increase in $TR_{90}$ was seen with dofetilide and sotalol, while isoproterenol induced a decrease in $TR_{90}$. Verapamil had no effect on $TR_{90}$ up to 222× the fETPC.

Aspects of the present specification may also be described as follows:

1. A method for predicting at least one of a drug-induced inotropic risk and a pro-arrhythmia risk in connection with an at least one drug, based on a select at least one contractility parameter associated with an at least one heart, the method comprising the steps of: implementing a user application residing in memory on an at least one computing device, the at least one computing device configured for receiving and processing select data obtained by an at least one monitoring device positioned and configured for obtaining data related to the at least one heart; after the at least one drug has been administered to the at least one heart, determining whether the at least one drug has taken appropriate effect on the at least one heart; upon determining that the at least one drug has taken appropriate effect on the at least one heart: upon determining that the at least one heart consists of cell-based assays, obtaining at multiple pre-determined intervals for a pre-determined period of time, via the user application in communication with the at least one monitoring device, at least one contractility parameter comprising cardiomyocyte contractility transients including at least one of a fractional sarcomere shortening ("$S_{FS}$"), a time to 90% relaxation ("$TR_{90}$"), an after-contraction ("AC"), a contractility escape type 1 ("CE1"), and a contractility escape type 2 ("CE2"); and upon determining that the at least one heart consists of organ-based or tissue-based assays, obtaining at multiple pre-determined intervals for a pre-determined period of time, via the user application in communication with the at least one monitoring device, at least one contractility parameter related to trabeculae force of contraction including at least one of a maximum amplitude of force of contraction ("MAC"), a time to 70% relaxation ("$TR_{70}$"), a time to 90% relaxation ("$TR_{90}$"), an after-contraction ("AC"), and a contraction escape ("CE"); calculating, via the user application, a delta for each of the at least one obtained contractility parameter; determining, via the user application, whether any of the at least one obtained contractility parameter has a delta that equals or exceeds an at least one risk threshold value associated with each said at least one obtained contractility parameter; upon determining, via the user application, that a pre-determined number of the at least one obtained contractility parameter each has a delta that equals or exceeds the associated at least one risk threshold value, concluding that there is at least one of a drug-induced inotropic risk and a pro-arrhythmia risk in connection with the at least one drug; and upon determining, via the user application, that a pre-determined number of the at least one obtained contractility parameter each has a delta that is less than the associated at least one risk threshold value, concluding that there is likely an absence of at least one of a drug-induced inotropic risk and a pro-arrhythmia risk in connection with the at least one drug.

2. The method according to embodiment 1, wherein the step of determining whether the at least one drug has taken appropriate effect on the at least one heart further comprises the step of determining whether the at least one drug has reached its plateau effect.

3. The method according to embodiments 1-2, wherein the step of obtaining at least one contractility parameter comprising cardiomyocyte contractility transients further comprises the step of obtaining at least one of a peak height, a maximum contraction velocity, a maximum contraction velocity time, a maximum relaxation velocity, a maximum relaxation velocity time, a time to peak, a time to 10% peak, and a time to 50% peak.

4. The method according to embodiments 1-3, wherein the step of obtaining at least one contractility parameter comprising cardiomyocyte contractility transients further comprises the step of obtaining a set of between five and 120 consecutive transients of said at least one contractility parameter comprising cardiomyocyte contractility transients.

5. The method according to embodiments 1-4, wherein the step of obtaining at least one contractility parameter related to trabeculae force of contraction further comprises the step of obtaining at least one of a peak amplitude, an amplitude height, a time to peak, a rise time, a fall time, a rise slope, a fall slope, a maximum slope, and a minimum slope.

6. The method according to embodiments 1-5, wherein the step of obtaining at least one contractility parameter related to trabeculae force of contraction further comprises the step of obtaining a set of between five and 120 consecutive transients of said at least one contractility parameter related to trabeculae force of contraction.

7. The method according to embodiments 1-6, further comprising the step of obtaining, via the user application in communication with the at least one monitoring device, at least one of a time to reaction ("TR") instability, a TR triangulation, a short-term variability ("STV") of TR, a TR alternans, a maximum TR dispersion, and an effective refractory period ("ERP") of TR.

8. The method according to embodiments 1-7, further comprising the step of obtaining a set of between five and 120 consecutive transients of said at least one of a time to reaction ("TR") instability, a TR triangulation, a short-term variability ("STV") of TR, a TR alternans, a maximum TR dispersion, and an effective refractory period ("ERP") of TR.

9. The method according to embodiments 1-8, further comprising the step of determining, via the user application, a number of consecutive transients to be obtained by the user application based on at least one of a type of drug being tested, a desired sensitivity of the prediction, and a desired specificity of the prediction.

10. The method according to embodiments 1-9, wherein the step of determining that a pre-determined number of the at least one obtained contractility parameter each has a delta that equals or exceeds the associated at least one risk threshold value, further comprises the step of, upon determining, via the user application, that at least one of the at least one obtained contractility parameter has a delta that equals or exceeds the associated at least one risk threshold value, concluding that there is at least one of a drug-induced inotropic risk and a pro-arrhythmia risk in connection with the at least one drug.

11. The method according to embodiments 1-10, wherein the step of determining that a pre-determined number of the at least one obtained contractility parameter each has a delta that equals or exceeds the associated at least one risk threshold value, further comprises the step of, upon determining, via the user application, that the delta associated with at least one of the after-contraction ("AC"), contractility escape type 1 ("CE1"), and contractility escape type 2 ("CE2") equals or exceeds the associated at least one risk threshold value, concluding that there is at least one of a drug-induced inotropic risk and a pro-arrhythmia risk in connection with the at least one drug.

12. The method according to embodiments 1-11, wherein the step of determining that a pre-determined number of the at least one obtained contractility parameter each has a delta that equals or exceeds the associated at least one risk threshold value, further comprises the step of, upon determining, via the user application, that none of the at least one obtained contractility parameter has a delta that equals or exceeds the associated at least one risk threshold value, concluding that there is likely an absence of at least one of a drug-induced inotropic risk and a pro-arrhythmia risk in connection with the at least one drug.

13. A drug-induced risk prediction system for predicting at least one of a drug-induced inotropic risk and a pro-arrhythmia risk in connection with an at least one drug, based on a select at least one contractility parameter associated with an at least one heart, the system comprising: an at least one computing device configured for receiving and processing select data obtained by an at least one monitoring device positioned and configured for obtaining data related to the at least one heart; wherein, the at least one computing device is configured for: after the at least one drug has been administered to the at least one heart, determining whether the at least one drug has taken appropriate effect on the at least one heart; upon determining that the at least one drug has taken appropriate effect on the at least one heart: upon determining that the at least one heart consists of cell-based assays, obtaining at multiple pre-determined intervals for a pre-determined period of time, via the at least one monitoring device, at least one contractility parameter comprising cardiomyocyte contractility transients including at least one of a fractional sarcomere shortening ("$S_{FS}$"), a time to 90% relaxation ("$TR_{90}$"), an after-contraction ("AC"), a contractility escape type 1 ("CE1"), and a contractility escape type 2 ("CE2"); and upon determining that the at least one heart consists of organ-based or tissue-based assays, obtaining at multiple pre-determined intervals for a pre-determined period of time, via the at least one monitoring device, at least one contractility parameter related to trabeculae force of contraction including at least one of a maximum amplitude of force of contraction ("MAC"), a time to 70% relaxation ("$TR_{70}$"), a time to 90% relaxation ("$TR_{90}$"), an after-contraction ("AC"), and a contraction escape ("CE"); calculating a delta for each of the at least one obtained contractility parameter; determining whether any of the at least one obtained contractility parameter has a delta that equals or exceeds an at least one risk threshold value associated with each said at least one obtained contractility parameter; upon determining that a pre-determined number of the at least one obtained contractility parameter each has a delta that equals or exceeds the associated at least one risk threshold value, concluding that there is at least one of a drug-induced inotropic and a pro-arrhythmia risk in connection with the at least one drug; and upon determining that a pre-determined number of the at least one obtained contractility parameter each has a delta that is less than the associated at least one risk threshold value, concluding that there is likely an absence of at least one of a drug-induced inotropic risk and a pro-arrhythmia risk in connection with the at least one drug.

14. The drug-induced risk prediction system according to embodiment 13, wherein the at least one heart is at least one of an ex vivo isolated heart, an isolated sample of cardiac tissue, and isolated cardiomyocytes.

15. The drug-induced risk prediction system according to embodiments 13-14, wherein the at least one monitoring device includes an ECG device positioned and configured for obtaining electrical activity associated with the at least one heart.

16. The drug-induced risk prediction system according to embodiments 13-15, wherein the at least one monitoring device includes a force transducer device positioned and configured for obtaining force activity associated with the at least one heart.

17. The drug-induced risk prediction system according to embodiments 13-16, wherein the at least one monitoring device includes a current amplifier device positioned and configured for obtaining electrical activity associated with the at least one heart.

18. The drug-induced risk prediction system according to embodiments 13-17, wherein the at least one monitoring device includes an optical device positioned and configured for obtaining visual data associated with contractions of the at least one heart.

19. The drug-induced risk prediction system according to embodiments 13-18, further comprising an at least one data storage device in selective communication with the at least one computing device and configured for storing said data obtained by the at least one monitoring device and processed by the at least one computing device.

20. The drug-induced risk prediction system according to embodiments 13-19, wherein while determining whether the at least one drug has taken appropriate effect on the at least one heart, the at least one computing device is further configured for determining whether the at least one drug has reached its plateau effect.

21. The drug-induced risk prediction system according to embodiments 13-20, wherein while obtaining at least one contractility parameter comprising cardiomyocyte contractility transients, the at least one computing device is further configured for obtaining at least one of a peak height, a maximum contraction velocity, a maximum contraction velocity time, a maximum relaxation velocity, a maximum relaxation velocity time, a time to peak, a time to 10% peak, and a time to 50% peak.

22. The drug-induced risk prediction system according to embodiments 13-21, wherein while obtaining at least one contractility parameter comprising cardiomyocyte contractility transients, the at least one computing device is further configured for obtaining a set of between five and 120 consecutive transients of said at least one contractility parameter comprising cardiomyocyte contractility transients.

23. The drug-induced risk prediction system according to embodiments 13-22, wherein while obtaining at least one contractility parameter related to trabeculae force of contraction, the at least one computing device is further configured for obtaining at least one of a peak amplitude, an amplitude height, a time to peak, a rise time, a fall time, a rise slope, a fall slope, a maximum slope, and a minimum slope.

24. The drug-induced risk prediction system according to embodiments 13-23, wherein while obtaining at least one contractility parameter related to trabeculae force of contraction, the at least one computing device is further configured for obtaining a set of between five and 120 consecutive transients of said at least one contractility parameter related to trabeculae force of contraction.

25. The drug-induced risk prediction system according to embodiments 13-24, wherein the at least one computing device is further configured for obtaining, via the at least one monitoring device, at least one of a time to reaction ("TR") instability, a TR triangulation, a short-term variability ("STV") of TR, a TR alternans, a maximum TR dispersion, and an effective refractory period ("ERP") of TR.

26. The drug-induced risk prediction system according to embodiments 13-25, wherein the at least one computing device is further configured for obtaining a set of between five and 120 consecutive transients of said at least one of a time to reaction ("TR") instability, a TR triangulation, a short-term variability ("STV") of TR, a TR alternans, a maximum TR dispersion, and an effective refractory period ("ERP") of TR.

27. The drug-induced risk prediction system according to embodiments 13-26, wherein the at least one computing device is further configured for determining a number of consecutive transients to be obtained based on at least one of a type of drug being tested, a desired sensitivity of the prediction, and a desired specificity of the prediction.

28. The drug-induced risk prediction system according to embodiments 13-27, wherein while determining that a pre-determined number of the at least one obtained contractility parameter each has a delta that equals or exceeds the associated at least one risk threshold value, the at least one computing device is further configured for, upon determining that at least one of the at least one obtained contractility parameter has a delta that equals or exceeds the associated at least one risk threshold value, concluding that there is at least one of a drug-induced inotropic risk and a pro-arrhythmia risk in connection with the at least one drug.

29. The drug-induced risk prediction system according to embodiments 13-28, wherein while determining that a pre-determined number of the at least one obtained contractility parameter each has a delta that equals or exceeds the associated at least one risk threshold value, the at least one computing device is further configured for, upon determining that the delta associated with at least one of the after-contraction ("AC"), contractility escape type 1 ("CE1"), and contractility escape type 2 ("CE2") equals or exceeds the associated at least one risk threshold value, concluding that there is at least one of a drug-induced inotropic risk and a pro-arrhythmia risk in connection with the at least one drug.

30. The drug-induced risk prediction system according to embodiments 13-29, wherein while determining that a pre-determined number of the at least one obtained contractility parameter each has a delta that equals or exceeds the associated at least one risk threshold value, the at least one computing device is further configured for, upon determining that none of the at least one obtained contractility parameter has a delta that equals or exceeds the associated at least one risk threshold value, concluding that there is likely an absence of at least one of a drug-induced inotropic risk and a pro-arrhythmia risk in connection with the at least one drug.

31. A non-transient computer readable medium containing program instructions for causing an at least one computing device to perform a method of predicting at least one of a drug-induced inotropic risk and a pro-arrhythmia risk in connection with an at least one drug, based on a select at least one contractility parameter associated with an at least one heart, the method comprising the steps of: after the at least one drug has been administered to the at least one heart, determining whether the at least one drug has taken appropriate effect on the at least one heart; upon determining that the at least one drug has taken appropriate effect on the at least one heart: upon determining that the at least one heart consists of cell-based assays, obtaining at multiple pre-determined intervals for a pre-determined period of time, via an at least one monitoring device positioned and configured for obtaining data related to the at least one heart, at least one contractility parameter comprising cardiomyocyte contractility transients including at least one of a fractional sarcomere shortening ("$S_{FS}$"), a time to 90% relaxation ("$TR_{90}$"), an after-contraction ("AC"), a contractility escape type 1 ("CE1"), and a contractility escape type 2 ("CE2"); and upon determining that the at least one heart consists of organ-based or tissue-based assays, obtaining at multiple pre-determined intervals for a pre-determined period of time, via the at least one monitoring device, at least one contractility parameter related to trabeculae force of contraction including at least one of a maximum amplitude of force of contraction ("MAC"), a time to 70% relaxation ("$TR_{70}$"), a time to 90% relaxation ("$TR_{90}$"), an after-contraction ("AC"), and a contraction escape ("CE"); calculating a delta for each of the at least one obtained contractility parameter; determining whether any of the at least one obtained contractility parameter has a delta that equals or exceeds an at least one risk threshold value associated with each said at least one obtained contractility parameter; upon determining that a pre-determined number of the at least one obtained contractility parameter each has a delta that equals or exceeds the associated at least one risk threshold value, concluding that there is at least one of a drug-induced inotropic risk and a pro-arrhythmia risk in connection with the at least one drug; and upon determining that a pre-determined number of the at least one obtained contractility parameter each has a delta that is less than the associated at least one risk threshold value, concluding that there is likely an absence of at least one of a drug-induced inotropic risk and a pro-arrhythmia risk in connection with the at least one drug.

32. The method according to embodiment 31, wherein the step of determining whether the at least one drug has taken appropriate effect on the at least one heart further comprises the step of determining whether the at least one drug has reached its plateau effect.

33. The method according to embodiments 31-32, wherein the step of obtaining at least one contractility parameter comprising cardiomyocyte contractility transients further comprises the step of obtaining at least one of a peak height, a maximum contraction velocity, a maximum contraction velocity time, a maximum relaxation velocity, a maximum relaxation velocity time, a time to peak, a time to 10% peak, and a time to 50% peak.

34. The method according to embodiments 31-33, wherein the step of obtaining at least one contractility parameter comprising cardiomyocyte contractility transients further comprises the step of obtaining a set of between five and 120 consecutive transients of said at least one contractility parameter comprising cardiomyocyte contractility transients.

35. The method according to embodiments 31-34, wherein the step of obtaining at least one contractility parameter related to trabeculae force of contraction further comprises the step of obtaining at least one of a peak amplitude, an amplitude height, a time to peak, a rise time, a fall time, a rise slope, a fall slope, a maximum slope, and a minimum slope.

36. The method according to embodiments 31-35, wherein the step of obtaining at least one contractility parameter related to trabeculae force of contraction further comprises the step of obtaining a set of between five and 120 consecutive transients of said at least one contractility parameter related to trabeculae force of contraction.

37. The method according to embodiments 31-36, further comprising the step of obtaining, via the at least one monitoring device, at least one of a time to reaction ("TR") instability, a TR triangulation, a short-term variability ("STV") of TR, a TR alternans, a maximum TR dispersion, and an effective refractory period ("ERP") of TR.

38. The method according to embodiments 31-37, further comprising the step of obtaining a set of between five and 120 consecutive transients of said at least one of a time to reaction ("TR") instability, a TR triangulation, a short-term variability ("STV") of TR, a TR alternans, a maximum TR dispersion, and an effective refractory period ("ERP") of TR.

39. The method according to embodiments 31-38, further comprising the step of determining a number of consecutive transients to be obtained based on at least one of a type of drug being tested, a desired sensitivity of the prediction, and a desired specificity of the prediction.

40. The method according to embodiments 31-39, wherein the step of determining that a pre-determined number of the at least one obtained contractility parameter each has a delta that equals or exceeds the associated at least one risk threshold value, further comprises the step of, upon determining that at least one of the at least one obtained contractility parameter has a delta that equals or exceeds the associated at least one risk threshold value, concluding that there is at least one of a drug-induced inotropic risk and a pro-arrhythmia risk in connection with the at least one drug.

41. The method according to embodiments 31-40, wherein the step of determining that a pre-determined number of the at least one obtained contractility parameter each has a delta that equals or exceeds the associated at least one risk threshold value, further comprises the step of, upon determining that the delta associated with at least one of the after-contraction ("AC"), contractility escape type 1 ("CE1"), and contractility escape type 2 ("CE2") equals or exceeds the associated at least one risk threshold value, concluding that there is at least one of a drug-induced inotropic risk and a pro-arrhythmia risk in connection with the at least one drug.

42. The method according to embodiments 31-41, wherein the step of determining that a pre-determined number of the at least one obtained contractility parameter each has a delta that equals or exceeds the associated at least one risk threshold value, further comprises the step of, upon determining that none of the at least one obtained contractility parameter has a delta that equals or exceeds the associated at least one risk threshold value, concluding that there is likely an absence of at least one of a drug-induced inotropic risk and a pro-arrhythmia risk in connection with the at least one drug.

In closing, regarding the exemplary embodiments of the present invention as shown and described herein, it will be appreciated that a drug-induced risk prediction system and associated methods of use are disclosed and configured for predicting at least one of a drug-induced inotropic risk and a pro-arrhythmia risk in connection with an at least one drug to be tested. Because the principles of the invention may be practiced in a number of configurations beyond those shown and described, it is to be understood that the invention is not in any way limited by the exemplary embodiments, but is generally directed to a drug-induced risk prediction system and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein. Similarly, as used herein, unless indicated to the contrary, the term "substantially" is a term of degree intended to indicate an approximation of the characteristic, item, quantity, parameter, property, or term so qualified, encompassing a range that can be understood and construed by those of ordinary skill in the art.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may comprise one or more modules that execute on one or more processors in a distributed, non-distributed, or multiprocessing environment.

The methods as described above may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multi-chip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A method for predicting a drug-induced pro-arrhythmia risk in connection with an at least one drug that has been administered to an at least one isolated primary adult cardiomyocyte from a human heart, based on an at least one after-contraction transient ("AC") associated with the at least one cardiomyocyte, the method comprising the steps of:
    implementing an at least one monitoring device positioned and configured for measuring data related to the at least one cardiomyocyte, wherein the at least one monitoring device is an optical device positioned and configured for measuring visual data associated with contractions of the at least one cardiomyocyte;
    implementing a user application residing in memory on an at least one computing device, the at least one computing device configured for receiving and processing select data obtained by the at least one monitoring device;
    measuring, via the at least one monitoring device, the effect of the at least one drug on the at least one cardiomyocyte;
    determining, via the user application, the at least one drug has taken effect on the at least one cardiomyocyte;
    applying a controlled external electrical stimulus to the at least one cardiomyocyte;
    measuring, via the at least one monitoring device, a sequence of at least 60 sarcomere contraction transients of the at least one cardiomyocyte;
    transmitting, via the at least one monitoring device, the measured sarcomere contraction transients to the user application;
    determining, via the user application, the presence of an after-contraction transient for each of the measured sarcomere contraction transients, wherein the after-contraction transient is a secondary peak in a late portion of a relaxation phase of the associated sarcomere contraction transient;
    calculating, via the user application, a delta corresponding to a quantity of measured sarcomere contraction transients containing an after-contraction transient;
    determining, via the user application, a drug-induced pro-arrhythmia risk in connection with the at least one drug wherein the delta equals or exceeds a pre-determined risk threshold value, said risk threshold value being one percent of the quantity of sarcomere contraction transients in the measured sequence; and
    determining, via the user application, a likelihood of an absence of a drug-induced pro-arrhythmia risk in connection with the at least one drug wherein the delta is less than the risk threshold value.

2. The method of claim 1, wherein the step of determining the at least one drug has taken effect on the at least one cardiomyocyte further comprises the step of determining the at least one drug has reached its plateau effect on the at least one cardiomyocyte.

3. The method of claim 1, further comprising the step of determining, via the user application, at least one of a peak height, a maximum contraction velocity, a maximum contraction velocity time, a maximum relaxation velocity, a maximum relaxation velocity time, a time to peak, a time to 10% peak, and a time to 50% peak for each of the measured sarcomere contraction transients.

4. The method of claim 1, wherein the step of measuring, via the at least one monitoring device, a sequence of at least 60 sarcomere contraction transients further comprises the step of measuring a sequence of at least 300 sarcomere contraction transients of the at least one cardiomyocyte.

5. The method of claim 1, further comprising the step of determining, via the user application, at least one of a peak amplitude, an amplitude height, a time to peak, a rise time, a fall time, a rise slope, a fall slope, a maximum slope, and a minimum slope for each of the measured sarcomere contraction transients.

6. The method of claim 1, further comprising the step of determining, via the user application, at least one of a time to reaction ("TR") instability, a TR triangulation, a short-term variability ("STV") of TR, a TR alternans, a maximum TR dispersion, and an effective refractory period ("ERP") of TR for the measured sarcomere contraction transients.

7. The method of claim 1, further comprising the step of determining, via the user application, a number of consecutive sarcomere contraction transients to be measured by the at least one monitoring device and subsequently transmitted to the user application based on at least one of a type of drug being tested, a desired sensitivity of the prediction, and a desired specificity of the prediction.

8. A method for predicting a drug-induced pro-arrhythmia risk in connection with an at least one drug that has been administered to an at least one isolated primary adult cardiomyocyte from a human heart, based on an at least one after-contraction transient ("AC") associated with the at least one cardiomyocyte, the method comprising the steps of:
    implementing an at least one monitoring device positioned and configured for measuring data related to the at least one cardiomyocyte, wherein the at least one monitoring device is an optical device positioned and configured for measuring visual data associated with contractions of the at least one cardiomyocyte;

implementing a user application residing in memory on an at least one computing device, the at least one computing device configured for receiving and processing select data obtained by the at least one monitoring device;

measuring, via the at least one monitoring device, the effect of the at least one drug on the at least one cardiomyocyte;

determining, via the user application, the at least one drug has taken effect on the at least one cardiomyocyte;

applying a controlled external electrical stimulus to the at least one cardiomyocyte;

measuring, via the at least one monitoring device, a sequence of at least 300 sarcomere contraction transients of the at least one cardiomyocyte;

transmitting, via the at least one monitoring device, the measured sarcomere contraction transients to the user application;

determining, via the user application, the presence of an after-contraction transient for each of the measured sarcomere contraction transients, wherein the after-contraction transient is a secondary peak in a late portion of a relaxation phase of the associated sarcomere contraction transient;

calculating, via the user application, a delta corresponding to a quantity of measured sarcomere contraction transients containing an after-contraction transient;

determining, via the user application, a drug-induced pro-arrhythmia risk in connection with the at least one drug wherein the delta equals or exceeds a pre-determined risk threshold value, said risk threshold value being three; and determining, via the user application, a likelihood of an absence of a drug-induced pro-arrhythmia risk in connection with the at least one drug wherein the delta is less than the risk threshold value.

* * * * *